United States Patent
Mercey

(10) Patent No.: US 9,746,467 B2
(45) Date of Patent: Aug. 29, 2017

(54) MICROSTRUCTURED CHIP FOR SURFACE PLASMON RESONANCE ANALYSIS, ANALYSIS DEVICE CONTAINING SAID MICROSTRUCTURED CHIP AND USE OF SAID DEVICE

(71) Applicant: Thibaut Mercey, Paris (FR)

(72) Inventor: Thibaut Mercey, Paris (FR)

(73) Assignee: PRESTODIAG, Villejuif (FR)

( * ) Notice: Subject to any disclaimer, the term of this patent is extended or adjusted under 35 U.S.C. 154(b) by 352 days.

(21) Appl. No.: 14/354,253

(22) PCT Filed: Oct. 25, 2012

(86) PCT No.: PCT/FR2012/052451
§ 371 (c)(1),
(2) Date: Apr. 25, 2014

(87) PCT Pub. No.: WO2013/060988
PCT Pub. Date: May 2, 2013

(65) Prior Publication Data
US 2014/0371093 A1    Dec. 18, 2014

(30) Foreign Application Priority Data
Oct. 26, 2011   (FR) ..................... 11 59716

(51) Int. Cl.
*G01J 3/44*       (2006.01)
*G01N 21/55*     (2014.01)
(Continued)

(52) U.S. Cl.
CPC ..... *G01N 33/54373* (2013.01); *G01N 21/553* (2013.01); *G01N 21/253* (2013.01);
(Continued)

(58) Field of Classification Search
CPC .......... G01N 33/54373; G01N 21/553; G01N 2201/02; G01N 2201/08; G01N 2469/00; G01N 21/253
(Continued)

(56) References Cited

U.S. PATENT DOCUMENTS

| 5,313,264 A | 5/1994 | Ivarsson et al. |
| 6,862,094 B2 | 3/2005 | Johansen |

(Continued)

FOREIGN PATENT DOCUMENTS

| EP | 2264438 A1 | 12/2010 |
| FR | 2860872 A1 | 5/2005 |

(Continued)

OTHER PUBLICATIONS

Coyle et al., "Localised Plasmons in Gold Photonic Nanocavities", Friday Morning, QELS 2002, QFB3 8:45am., p. 257.
(Continued)

*Primary Examiner* — Sunghee Y Gray
(74) *Attorney, Agent, or Firm* — Young & Thompson

(57) ABSTRACT

A microstructured chip (3; 33; 43; 53; 63) for surface plasmon resonance (SPR) analysis, taking the form of a solid formed by: a base (5; 77); an upper surface (4; 44), at least part of which is covered with a metal layer (2; 22; 42; 52; 62); and at least one side surface (55; 66). The chip is characterized in that the aforementioned upper surface is provided with micrometric zones intended to receive species to be analyzed and selected from among n protrusions and m cavities, and in that when n+m≥2 the zones are separated from one another by planar surfaces, with n varying between 1 and j, m varying between 0 and i, and j and i being integers.

8 Claims, 9 Drawing Sheets

(51) Int. Cl.
*C12M 3/00* (2006.01)
*G01N 33/53* (2006.01)
*G01N 33/554* (2006.01)
*C40B 30/04* (2006.01)
*C40B 60/12* (2006.01)
*G01N 33/543* (2006.01)
*G01N 21/552* (2014.01)
*G01N 21/25* (2006.01)

(52) U.S. Cl.
CPC ..... *G01N 2201/02* (2013.01); *G01N 2201/08* (2013.01); *G01N 2469/00* (2013.01)

(58) Field of Classification Search
USPC ............. 356/301, 445; 435/287.2, 7.1, 7.32; 436/501; 506/9, 39; 422/69
See application file for complete search history.

(56) References Cited

U.S. PATENT DOCUMENTS

| | | | |
|---|---|---|---|
| 7,551,286 B2 | 6/2009 | Tani et al. | |
| 7,576,863 B2 | 8/2009 | Weibel | |
| 7,678,584 B2 | 3/2010 | Guedon et al. | |
| 7,705,989 B2 | 4/2010 | Chaton et al. | |
| 2002/0115224 A1* | 8/2002 | Rudel | B01J 19/0046 436/164 |
| 2005/0213868 A1 | 9/2005 | Cunningham | |
| 2008/0198376 A1* | 8/2008 | Poponin | G01N 21/658 356/301 |
| 2010/0227769 A1 | 9/2010 | Schulz et al. | |
| 2011/0120554 A1* | 5/2011 | Chhajed | C09D 1/00 136/259 |
| 2011/0212512 A1* | 9/2011 | Wang | B82Y 20/00 435/288.7 |
| 2011/0267610 A1* | 11/2011 | Hu | G01N 21/7746 356/301 |
| 2012/0113419 A1* | 5/2012 | Wang | B82Y 15/00 356/301 |
| 2012/0157804 A1* | 6/2012 | Rogers | A61B 5/0422 600/345 |
| 2012/0170033 A1* | 7/2012 | Zhu | G01N 21/658 356/301 |

FOREIGN PATENT DOCUMENTS

| | | |
|---|---|---|
| JP | 2003-215027 A | 7/2003 |
| JP | 2005-337771 A | 12/2005 |
| JP | 2005337771 A | 12/2005 |
| WO | 2009021964 A2 | 2/2009 |
| WO | 2011014176 * | 2/2011 ............ B82Y 15/00 |

OTHER PUBLICATIONS

Turker et al., "Grating coupler integrated photodiodes for plasmon resonance based sensing", Lab Chip, 2011, vol. 11, pp. 282-287.
Giudicatti et al., "Plasmonic resonances in nanostructured gold/polymer surfaces by colloidal lithography", Physica Status Solidi A, 2010, vol. 207, No. 4, pp. 935-942.
Mannelli et al., "Bioadhesive nanoareas in antifouling matrix for highly efficient affinity sensors", Proc. of SPIE, 2008, vol. 7035, 70350Y, XP002665168.
Rooney et al., "Designing a curved surface SPR device", Sensors and Actuators B, 2006, vol. 114, pp. 804-811.
Valsesia, Andrea, "Fabrication of nanostructured surfaces for the development of advanced biointerfaces", Scientifica Acta 1, 2007, No. 1, pp. 153-157, XP002665167.
International Search Report, dated Jan. 28, 2013, from corresponding PCT application.

* cited by examiner

MICROSTRUCTURED CHIP FOR SURFACE PLASMON RESONANCE ANALYSIS, ANALYSIS DEVICE CONTAINING SAID MICROSTRUCTURED CHIP AND USE OF SAID DEVICE

FIELD OF THE INVENTION

The present invention relates to a microstructured chip for surface plasmon resonance analysis, to an analysis device containing said microstructured chip, to a method of analysis and to the uses of said device.

PRIOR ART

Surface plasmon resonance (or SPR) is an optical technique which makes it possible to detect fine variations in physical properties in the immediate vicinity of a surface. This technique is especially known for making it possible to monitor biomolecular interactions in real time, and without labeling (fluorescent or radioactive dye, for example). It makes it possible in particular to describe and quantify interactions between ligands immobilized on a surface and analytes in solution in a sample.

SPR is a physical phenomenon of collective excitation of the electrons of a metal on a metal-dielectric medium interface (said dielectric medium being typically a liquid medium or a gas). For a particular polarization of the incident light (transverse magnetic, or "TM", polarization) on this interface (also referred to as "surface" in the rest of the text) and for an angle known as the "plasmon resonance angle", a resonance phenomenon occurs which is reflected by the coupling of the incident light energy to a surface wave (known as "surface plasmon") propagating parallel to the interface. This physical phenomenon is reflected by a drop in the intensity of the light reflected by the surface. This excitation takes place only for angles of incidence on the surface above the critical angle of total reflection (which can only exist when a radiation goes from a more refringent medium having an optical index n1 to a less refringent medium having an optical index n2, with n1>n2). In this case, the surface plasmon will "probe" the optical thickness at the surface of the metal, on the dielectric medium side, the optical thickness being defined as the product of the refractive index multiplied by the thickness. When these conditions come together, it can then be said that the surface is sensitive to the plasmon effect.

Typically, an incident radiation arrives according to a given angle of incidence on one of the side faces of a chip (generally a prism in the prior art, since it is the simplest method for coupling light on the sensitive surface), one of the faces of which is covered with a metal layer, and said incident radiation is refracted when it enters the prism (owing to the difference in optical index between the medium constituting the prism and the preceding optical medium, generally air) and is reflected on said metal surface. This configuration is well-known to those skilled in the art as the Kretschmann configuration (E. Kretschmann, *The determination of the Optical Constants of Metals by Excitation of Surface Plasmons, Z Physik* 241:313-324 (1971)). Equivalent configurations also exist when the prism is replaced with a diffraction network for coupling the light (Raether configuration: H. Raether in "*Surface Polaritons*", eds. Agranovich and Mills, North Holland Pubi. Comp., Amsterdam, 1982).

The SPR phenomenon can also make it possible to study biomolecular interactions. In this case, ligands are pre-immobilized on the metal surface of the prism in defined zones. Thus, any subsequent attachment of other molecules with these ligands will locally modify the optical thickness at the level of said defined zones, and will therefore cause variations in the resonance conditions and therefore a shift in the resonance angle. This shift is, as a first approximation, proportional to the amount of biomaterial which has come to interact with the ligands. Thus, small molecules will cause a small shift in the angle of incidence, whereas larger molecules will bring about a greater angular shift. Studying the variations in optical reflectivity associated with the resonance phenomenon will make it possible to detect and measure biomolecular interactions and their change over time at the level of the defined zones.

In addition, other optical methods also make it possible to perform such physical phenomena without labeling (resonant mirror, interferometry, surface acoustic waves, quartz microbalance), but these techniques require equipment which is expensive and unsuitable for actual industrial applications.

Technical Problem

The current SPR systems are bulky, expensive and difficult to implement and do not therefore make it possible to carry out analyses at low costs. Indeed, most of the systems currently sold require complicated measurement strategies and allow measurements only on a very precise (virtually point-like) zone of the surface. The devices which enable analyses of several zones in parallel are very complex and have moving mechanical parts, thus making the system bulky and difficult to use.

For this reason, for several years, a great deal of scientific research has been dedicated to the development of effective, economical SPR optical devices which are easy to use.

Document U.S. Pat. No. 5,313,264 (Ivarsson et al) describes an SPR device using an "angular" interrogation in which the surface to be studied is excited with a convergent beam and the intensity of the reflected beam is observed on a detector. However, this technique does not make it possible to study several zones in parallel, unless several detectors are juxtaposed (reference is made to an essentially "single-point" analysis).

The document "Designing a curved surface SPR device, J. Rooney and E. A. H. Hall, Sensors and Actuators B 114 (2006) 804-811" describes a device which makes it possible to detect a biomolecular interaction on a concave curve spherical substrate. Although said document suggests juxtaposing said device 8 times, the detection elements of the device are also multiplied 8 times, which makes the final device expensive and bulky.

Documents U.S. Pat. No. 6,862,094 (Johansen et al) and U.S. Pat. No. 7,576,863 (Weibel et al) describe an SPR device which uses, not an angular interrogation, but a wavelength interrogation using a monochromator or a source of white light. These devices make it possible to study several biomolecular interactions in parallel, but comprise moving parts, which increases the maintenance operations on the system, and therefore the overall cost for the user.

There are also SPR devices which make it possible to perform imaging and to monitor, at fixed angle of incidence and fixed wavelength, the change in biomolecular interactions in defined zones on a chip. Documents U.S. Pat. No. 7,678,584 (Guédon et al), U.S. Pat. No. 7,576,863 (Weibel et al) and U.S. Pat. No. 7,551,286 (Tani et al) present such SPR devices. Although these devices make it possible to analyze several interactions in parallel, they have moving parts or do not enable a fine analysis of the interaction when no part moves.

Furthermore, in all the devices previously described, it is virtually impossible to study at the same time, on one and the same chip, biological species of different sizes since the detection sensitivity depends on the size of the object sought, and one and the same angle of analysis cannot be optimized to detect both small molecules (diameter of about a few nm to a few tens of nm) and bulky elements, for instance bacteria (diameter of about a few hundred nm to a few w). Added to this is the fact that the angular measurement dynamics, fixed by design for the systems currently available, do not allow sufficient flexibility for studying biological species of very different natures or concentrations. Indeed, the optimum angular position for studying the biomolecular interactions on each defined zone of a chip may be different and is linked to (at least) three different parameters, namely (i) the type of surface chemistry used for the immobilization of the capture biological species, (ii) the (optical) thickness of the defined zones to the analysis thus formed and (iii) the type of target that will potentially interact with the immobilized species (for example ligands).

Thus, the optimum sensitivity of the plasmon, and also its angular measurement dynamics, will remain inaccessible for certain prior art devices, or else it will be necessary to set up much more sophisticated and expensive analysis strategies: moving mobile parts, or else a more complex imaging system, which requires recurring adjustments and makes the devices complicated to control and to use.

Furthermore, all the devices previously described use chips which are expensive by virtue of their fabrication process. Moreover, since the majority of devices are "single-point" devices, the price per analysis point is high.

Moreover, mention may also be made, in the prior art, of document WO 2009/021964 A2 (Maccraith et al) which describes an optical platform intended for detecting analytes by fluorescence. In said document, the upper planar surface of a network of protuberances of paraboloid form is coated with a metallic film and then functionalized with biological species. A fluorescence signal is then excited by virtue of a plasmonic effect generated by the paraboloid geometry of the protuberances, which makes it possible to obtain an incident beam on said metal-film-coated planar surface above the critical angle.

However, in said document, no information can be directly deduced from the characteristics of the plasmon wave itself, since it is used only for the indirect emission of light by luminescence. Furthermore, the working detection surface is a metal-film-coated planar surface, and makes it possible only to carry out an analysis at a precise angle of θ.

Finally, there also exists, in the prior art, numerous documents describing chips which have nanostructures at their surface, and some of which use the localized surface plasmon resonance (LSPR) physical phenomenon. By way of example, the document "*Grating coupler integrated photodiodes for plasmon resonance based sensing*, B. Turker et al., *Conference on lasers and Electro-Optics* 2011" describes biochips which have at their surface nanostructures arranged according to a periodic network. This network of nanostructures is used for coupling incident light to the plasmon wave of the metal/dielectric interface of the network. The document "Localised plasmons in gold photonic nanocavities, S. Coyle et al., Quantum Electronics and Laser Science Conference 2002" presents, for its part, a nanostructured surface with gold nanocavities. These gold nanocavities involve the localized surface plasmon resonance (LSPR) physical phenomenon which differs from the SPR phenomenon and which leads to an amplification of the plasmonic signals.

Thus, in the abovementioned two documents, not only is the production of networks and cavities on a nanometric scale difficult, but it is also necessary to make use of mobile parts for evaluating the variation in reflectivity of the metallic layer according to the angle of incidence of the light beam.

There is therefore a real need for a compact, economical SPR device which does not have any moving parts, which is simple to use and which makes it possible to analyze several interactions in parallel, with a suitable and optimized measurement sensitivity.

DESCRIPTION OF THE INVENTION

The present inventor has found that a device for SPR analysis comprising a microstructured chip which has a particular architecture makes it possible to satisfy these requirements.

The term "chip" or "microstructured chip" will be used without distinction in the rest of the text.

The term "radiation" or "beam" will be used without distinction in the rest of the text.

Figure 1:
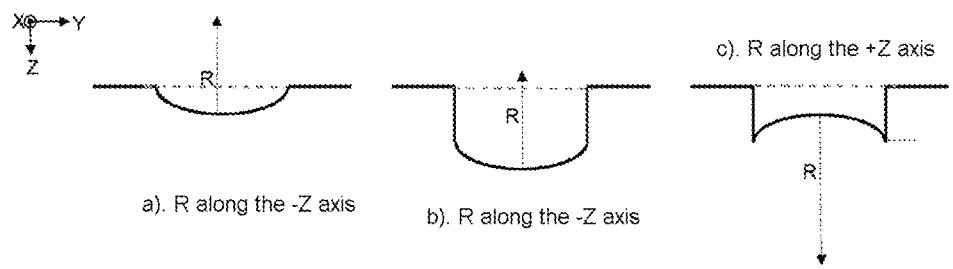
FIG. 1 represents a sectional view of the cavities according to various embodiments of the invention.

MICROSTRUCTURED CHIP

A first subject of the invention is a microstructured chip for surface plasmon resonance (SPR) analysis which is in the form of a solid consisting of a base, of an upper face, at least one part of which is covered with a metal layer, and of at least one side face, characterized in that:

- said upper face is provided with at least two zones of micrometric size chosen from at least one cavity and/or at least one protuberance intended to receive species to be analyzed; said zones being separated from one another by planar surfaces; and
- at least one of said zones is different from the others.

The term "microstructured chip" is intended to mean a chip which has zones of micrometric size intended to receive species to be analyzed. Thus, the chip is not necessarily of micrometric size, but comprises zones which are of micrometric size.

The term "zones of micrometric size" is intended to mean zones which have at least two dimensions out of three that are of micrometric size, said micrometric dimensions ranging from 1 μm to 1000 μm, and preferentially from 10 μm to 500 μm.

The third dimension of the zone is not therefore necessarily micrometric and can exhibit distances of, for example, between 1 mm and 20 mm, preferably between 1 mm and 10 mm.

The zones according to the invention exhibit particular geometries in the form of cavities and/or of protuberances which will be subsequently described. It is at the level of these zones covered with a metal layer that the plasmon effect will be observed.

According to the invention, the chip comprises a number of zones of between 2 and 500 000, preferably between 10 and 10 000 and more preferentially between 25 and 400.

According to the invention, at least one part of the upper face is coated with the metal layer. It represents the working detection surface (also subsequently referred to as sensitive surface).

According to the invention, at least two zones of micrometric size, chosen from at least one cavity and/or at least one protuberance, are coated with the metal layer.

According to one particular embodiment, the upper face of the chip is entirely covered with the metal layer.

Thus, according to one particular embodiment combined with the preceding one, not only the zones but also the planar surfaces separating said zones are intended to receive species to be analyzed.

In order to facilitate the description which follows, the direct orthonormal reference frame (XYZ) is used in which the planar surfaces separating the zones are parallel to the plane (XY) and in which the Z axis is oriented downward.

The term "planar surfaces" is intended to mean planar or substantially planar surfaces which may exhibit some defects.

The planar surface separating two zones intended to receive species to be analyzed is referred to as inter-zone surface. Thus, the following terms will be used without distinction: planar surfaces or inter-zone surfaces or else inter-zone planar surfaces. More specifically:

- when the planar surface separates two zones which are cavities, the term inter-cavity surface is used;
- when the planar surface separates two zones which are protuberances, the term inter-protuberance surface is used; and
- when the planar surface separates a zone which is a cavity and another zone which is a protuberance, the term inter-cavity-protuberance surface is used.

According to one embodiment, the zones are arranged in the form of a matrix on the upper face of the chip. Thus, the planar surfaces separate the zones both along the X axis and along the Y axis.

According to another embodiment, the zones are arranged in the form of continuous gutters along the upper face of the chip. Thus, according to this embodiment, the planar surfaces separate the zones on the X axis or along the Y axis.

According to one embodiment, the zones are separated by a distance D along the Y axis and by a distance D' along the X axis by the planar surfaces (or inter-zone surfaces); D and D' being between 0 μm (in the case of a continuous gutter along one of the X or Y axes) and 5 mm, preferably between 50 μm and 5 mm, preferably between 200 and 1000 μm and particularly preferably between 300 and 700 μm.

According to one embodiment, the zones are separated by a center-to-center CTC distance of between 10 μm and 25 000 μm, preferably between 50 μm and 5000 μm and more preferentially between 100 μm and 1000 μm.

According to one embodiment, the planar surfaces are in planes parallel to the plane (XY); the upper face is then in the form of staircase steps.

According to another embodiment, the planar surfaces are in the same plane (XY) (i.e. Z is constant).

The expression "at least one of said zones is different from the others" is intended to mean:

- at least one zone having a different nature compared with the other zones of the chip; and/or
- at least one zone having a different dimension compared with the other zones of the chip; and/or
- at least one zone having a different orientation compared with the other zones of the chip; and/or
- at least one distance between an inter-zone surface and the base of the chip is different from the other inter-zone and base distances of the chip. The expression "distances between an inter-zone surface and the base of the chip" makes reference to the heights of the chip, i.e. the length of the perpendicular connecting the inter-zone surface and the base or an extension of the base.

The term "different nature" is intended to mean either a zone which is in the form of a cavity, or a zone which is in the form of a protuberance.

The term "different dimension" is intended to mean a zone which has, for example, a length L which is different and/or a width W which is different and/or a diameter d which is different and/or a mean radius of curvature R which is different from the other zones.

It should thus be noted that a zone Z1 which has the same geometry as another zone Z2 (for example, Z1 and Z2 being rectangular in shape with Z1 having a width W1 and a length L1, and Z2 having a width W2 and a length L2) but which has different dimensions (for example, $W1=W2$ and $L1<L2$) would be considered, for the purposes of the invention, to be different from the zone Z2.

The term "different orientation" is intended to mean a zone Z1' which exhibits a tilt of an angle $\beta1'$ relative to an adjacent planar surface, which is different from that of another zone of the chip, Z2', which has a tilt of an angle $\beta2'$ with $\beta1' \neq \beta2'$.

Thus, according to one embodiment, the chip is provided solely with zones which are cavities. In this case, since the zones are of the same nature, necessarily at least one of the cavities has a dimension different from the others and/or an orientation different from the others and/or at least one of the distances between the inter-cavity surfaces and the base of the chip is different.

According to another particular embodiment, the chip is provided solely with zones which are protuberances. In this case, since the zones are of the same nature, necessarily at least one of the protuberances has a dimension different from the others and/or an orientation different from the others and/or at least one of the distances between the inter-protuberance surfaces and the base of the chip is different.

Finally, according to yet another particular embodiment, the chip is provided with zones of which at least one is a cavity and another is a protuberance. In this particular embodiment, one zone differs from another only by virtue of its nature.

According to one embodiment, when the chip comprises at least one cavity and at least one protuberance, then at least one of the cavities and/or protuberances has a dimension different from the others and/or an orientation different from the others and/or at least one of the distances between the inter-protuberance and/or inter-cavity and/or inter-cavity-protuberance surfaces and the base of the chip is different.

The term "cavity" is intended to mean a hollow in the upper face of the chip, said hollow being between two planar surfaces (also referred to as inter-zone surfaces).

The cavity can be defined either in three dimensions (XYZ reference frame) or in two dimensions (section in one plane).

Thus, the term "cavity" is given to a volume of which all the coordinates are in an imaginary plane connecting the two inter-zone planar surfaces adjacent to said cavity.

The cavity will subsequently be described in the plane (YZ).

Thus, a cavity according to the invention, described in the plane (YZ), is defined by at least one curve having a mean radius of curvature R and/or at least one straight line.

When the cavity is defined only by a curve, then the curve is necessarily concave (i.e. radius of curvature along the −Z axis).

When the cavity is defined by at least one curve and at least one straight line, then the curve may be either concave or convex (i.e. radius of curvature along the +Z axis).

According to one particular embodiment, the cavity is defined by two straight lines separated by a curve.

According to one particular embodiment combined with the preceding one, the two straight lines are parallel.

According to another embodiment which can be combined with the preceding one, the two straight lines have different dimensions.

The term "protuberance" is intended to mean an outgrowth on the upper face of the chip, said outgrowth being between two planar surfaces (also referred to as inter-zone surfaces).

The protuberance can be defined either in 3 dimensions (XYZ reference frame) or in two dimensions (section in one plane).

Thus, the term "protuberance" is given to a volume of which all the coordinates are above an imaginary plane connecting the two inter-zone planar surfaces adjacent to said protuberance.

The protuberance will subsequently be described in the plane (YZ).

Thus, a protuberance according to the invention, described in the plane (YZ), is defined by at least one curve which has a mean radius of curvature R and/or at least one straight line.

When the protuberance is defined only by a curve, then the curve is necessarily convex (i.e. radius of curvature along the +Z axis).

When the protuberance is defined by at least one curve and at least one straight line, then the curve may be either concave (i.e. radius of curvature along the −Z axis), or convex.

According to one particular embodiment, the protuberance is defined by two straight lines separated by a curve.

According to one particular embodiment combined with the preceding one, the two straight lines are parallel.

According to another embodiment which can be combined with the preceding one, the two straight lines have different dimensions.

Thus, according to one particularly preferred embodiment, the zones of the chip (cavities and/or protuberances), described in the plane (YZ), are defined only by a curve having a mean radius of curvature R (concave for a cavity and convex for a protuberance); the radius of curvature R being between 0.1 mm and 600 mm, preferably between 0.3 mm and 300 mm.

By way of example, mention may be made of cavities and/or protuberances of hemispherical, semi-elliptical or semi-cylindrical shape (reference frame (XYZ)).

According to one preferred embodiment of the invention, the cavities and/or the protuberances have a semi-cylindrical shape in the reference frame (XYZ).

According to one particular embodiment, the radius of curvature of the zones (i.e. of the cavities and/or of the protuberances) is perpendicular to the plane (XY), i.e. along the Z axis.

According to another embodiment, the radius of curvature of the zones is not perpendicular to the plane (XY) (i.e. the cavities and/or protuberances have a tilt).

According to the invention, the base of the chip may be a planar or curved surface, or a ridge, or an apex.

According to one preferred embodiment, the base of the chip is a planar surface which is preferably parallel to the planar surfaces (also referred to as inter-zone surfaces).

According to another embodiment which can be combined with the preceding one, the planar surfaces are in the same plane (XY). In other words, if the base is parallel to said planar surfaces, the distances between the planar surfaces and the base of the chip are identical. In this case, it is said that the upper face is parallel to the base.

According to another embodiment, the planar surfaces are in multiple planes parallel to the plane (XY). In other words, if the base is parallel to said planar surfaces, the distances between the planar surfaces and the base of the chip are different (upper face in the form of a staircase step).

According to the invention, the side face(s) of the chip may be planar (perpendicular or not perpendicular to the base and/or to the upper face of the chip) or curved.

According to one preferred embodiment, the side face(s) of the chip is (are) planar.

According to another preferred embodiment, at least one side face of the chip is perpendicular to the base and/or to the upper face.

According to one particular embodiment of the invention, the chip is joined to a prism well-known from the prior art.

Thus, according to one particular embodiment, the chip is in the form of a parallelepiped (i.e. a chip which has planar surfaces in the same plane (XY) and a base parallel to said planar surfaces). According to this embodiment, the heights of the side surfaces have small dimensions of about from 0.1 mm to 20 mm, preferably from 1 mm to 10 mm.

The term "species to be analyzed" is intended to mean, for example, materials, gases or biological species such as single-stranded or double-stranded DNA, proteins, bacteria, toxins, viruses, mycoplasmas, chemical agents or any other biological or chemical species capable of interacting with other biological or chemical species.

According to one preferred embodiment, the species to be analyzed are biological species, such as pathogenic bacteria, for instance *Salmonella* spp., *Listeria monocytogenes, Clostridium difficile*, or else *Campylobacter* spp.

The present inventor has demonstrated that it is possible, by using the chip according to the invention, to advantageously study shiga toxin-producing *Escherichia coli* (STEC) strains, since it enables the simultaneous analysis of large molecules (bacteria themselves), but also of small toxins that they produce.

According to another preferred embodiment of the invention, the cavities and/or protuberances are functionalized with various biomarker-specific monoclonal antibodies.

FIG. 1 represents a section along the plane (ZY) of a cavity according to various embodiments. In each of these figures, the cavities represented by a surface in the plane (XY) (or by a volume in the XYZ reference frame), all the points of which lie below (positive Z) an imaginary straight line represented by dashes (or imaginary plane in the XYZ reference frame for a volume) connecting the two planar surfaces adjacent to the cavity:
- in case a): the cavity is defined solely by a concave-shaped curve with a radius of curvature R (i.e. having a radius of curvature along the −Z axis);
- in case b): the cavity is defined by two parallel straight lines separated by a concave-shaped curve with a radius of curvature R;
- in case c): the cavity is defined by two parallel straight lines separated by a curve with a radius of curvature R of convex shape (i.e. having a radius of curvature along the +Z axis).

Figure 2:
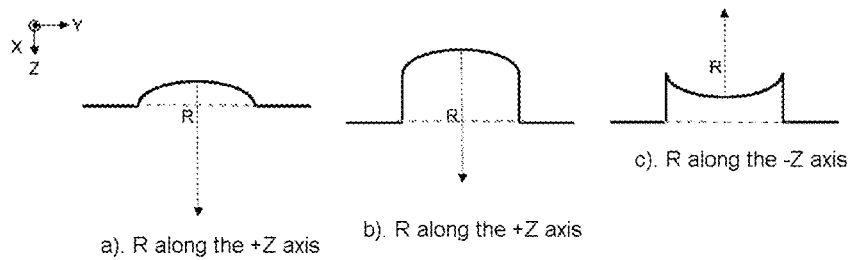
FIG. 2 represents a sectional view of the protuberances according to various embodiments of the invention.

FIG. 2 represents a section along the plane (ZY) of a protuberance according to various embodiments. In each of these figures, the protuberance is represented by a surface in the plane (XY) (or by a volume in the XYZ reference frame), all the points of which are located above (negative Z) an imaginary straight line represented by dashes (or imaginary plane in the XYZ reference frame for a volume) connecting the two planar surfaces adjacent to the protuberance:
- in case a): the protuberance is defined solely by a convex-shaped curve with a radius of curvature R (i.e. having a radius of curvature along the +Z axis);
- in case b): the protuberance is defined by two parallel straight lines separated by a curve with a radius of curvature R of convex shape;
- in case c): the protuberance is defined by two parallel straight lines separated by a curve with a radius of curvature R of concave shape (i.e. having a radius of curvature along the −Z axis).

Figure 3:
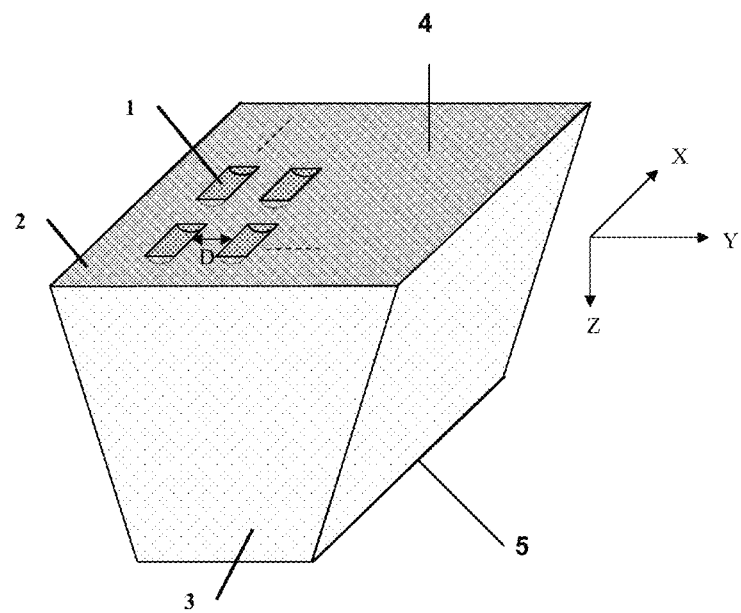
FIG. 3 represents a microstructured chip according to the invention which has cavities arranged in the form of a matrix.

FIG. 3 represents a microstructured chip 3, the upper face 4 of which, comprising the inter-cavity planar surfaces, is parallel to the base 5 of the chip 3. The upper face 4 is covered with a metal layer 2 and is provided with cavities 1 sensitive to the plasmon effect, intended to receive species to be analyzed.

In FIG. 3, the cavities 1 are separated from one another by a distance D along the Y axis and by a distance D' along the X axis, by planar surfaces (also referred to as inter-cavity surfaces).

The microstructured chip 3 can be made of any type of material which allows the propagation of light. Mention may be made, for example, of glass, a crystal or plastics.

According to one preferred embodiment, for cost reasons, the chip 3 is made of plastic(s), for instance PMMA (poly (methyl methacrylate)), PC (polycarbonate), PS (polystyrene), SU-8 (epoxy-based negative photosensitive resin) or PDMS (polydimethylsiloxane).

According to one particular embodiment, when the chip is joined to a prism, it may be made of a material different from that of the prism.

The metal layer 2 which covers the upper layer 4 of the chip 3 (and particularly the cavities 1) can be made of various metals such as gold, silver, platinum or aluminum.

According to one preferred embodiment, the metal layer is made of gold because of the very good anticorrosive properties of the latter.

The thickness of the metal layer 2 is between 10 and 200 nm, preferably between 30 and 100 nm and even more preferentially between 40 nm and 50 nm.

According to another embodiment combined with the preceding ones, a thin layer of chromium is used as a layer for preattachment of the gold to the upper face 4 of the chip 3.

Figure 4:
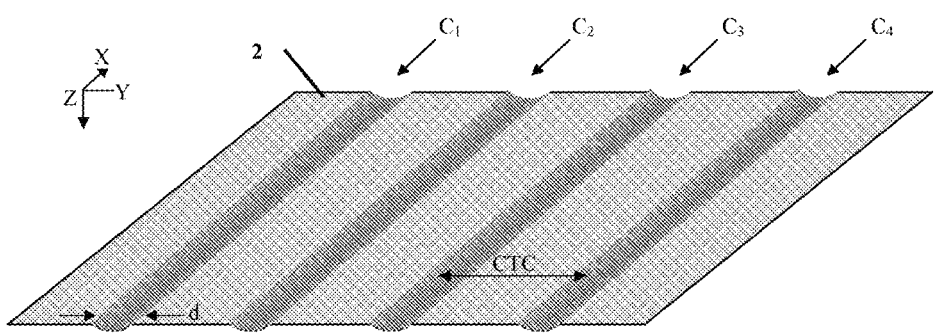
FIG. 4 represents the upper face of a microstructured chip according to the invention which has cavities arranged in the form of gutters along the X axis.

FIG. 4 represents the upper face of a microstructured chip according to the invention which is entirely covered with a metal layer 2; said microstructured chip is provided with cavities which are arranged in the form of gutters along the X axis, thus forming four columns $C_1$-$C_4$. In FIG. 4, d represents the diameter of the gutter and CTC represents the center-to-center distance between two successive gutters.

The chip according to the invention makes it possible to adjust the sensitivity of each zone (i.e. of each cavity and/or protuberance) in order to study very different biological species.

Figure 5:
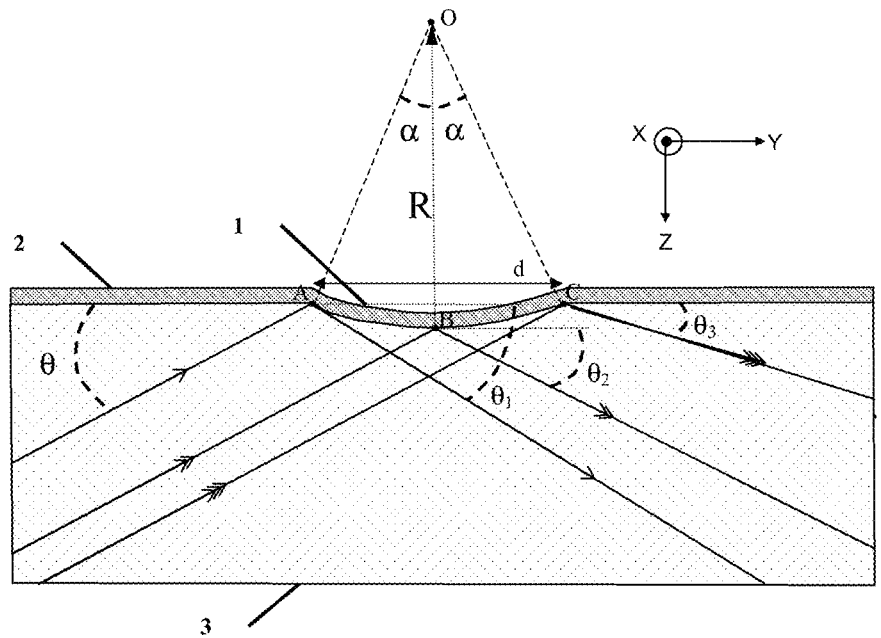
FIG. 5 represents a sectional view of a cavity without tilt, irradiated by a collimated and polarized monochromatic incident radiation.

According to one embodiment, at least one of said zones has a radius of curvature different from the others. FIG. 5 represents an enlargement of a sectional view of FIG. 3 of the curved-surface cavity 1 of the chip (covered with the metal layer 2) which is irradiated by a collimated monochromatic beam which has an angular incidence θ and is linearly polarized following TM polarization.

The cavity, which is semi-cylindrical in shape (in the XYZ reference frame), and which has a surface defined by a single curve (in the plane ZY) in FIGS. 3 and 5, is characterized by its radius of curvature R and by the two half-angles α (thus defining a total angle of 2α).

The radius of curvature R and the half-angle α will thus define the length of the chord d, or else the diameter of said cavity.

Owing to the reflection on the sensitive surface (or cavity 1), the angle of incidence on the two ends A and C will be respectively, for a mean angle of incidence of the collimated beam of θ, $\theta_1=\theta+2\alpha$, $\theta_2=\theta$ and $\theta_3=\theta-2\alpha$. Thus, the beam reflected ($\theta_1$ for the point A, $\theta_2$ for the point B, $\theta_3$ for the point C) by said cavity 1 has an angular width Δθ ($\Delta\theta=\theta_1-\theta_3$) equal to 4α, centered about the angle θmean (corresponding to the angle $\theta_2$ in FIG. 5).

The choice of the radius of curvature R of each cavity and/or protuberance of the chip according to the invention is very important since it will determine, according to the essential physical parameters (optical index of the chip $n_p$, optical index of the external dielectric medium $n_e$, mean angle of incidence of the collimated beam θ and the size of the biological species that it is desired to analyze), the sensitivity and the angular dynamics of the measurement for each cavity and/or protuberance.

The expression "angular dynamics of the measurement" is intended to mean the angular range that it will be possible to visualize during the analyses.

The term "sensitivity" is intended to mean the smallest variation in optical thickness that it will be possible to measure on the sensitive surface.

Indeed, if the radius of curvature is very large, this will draw closer to a plane, therefore the angles $\theta_1$ and $\theta_3$ will be very close (the angular range of analysis $\Delta\theta$ will therefore be very small), making this configuration particularly suitable for the analysis of small molecules (i.e. good sensitivity). Conversely, a very small radius of curvature will make it possible to observe the plasmon curve in its entirety, with admittedly a measurement sensitivity which is lower, but more suitable for the analysis of large molecules.

According to another embodiment which can be combined with the preceding one, at least one of said zones exhibits a tilt of an angle β.

According to this embodiment, the radius of curvature is deflected relative to the Z axis.

Figure 6:
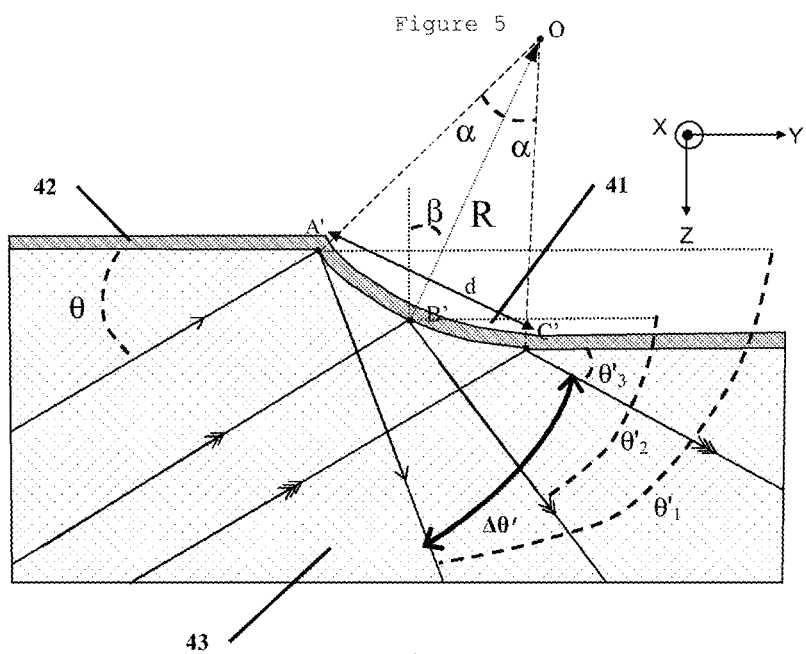
FIG. 6 represents a sectional view of a cavity which has a tilt of an angle β, irradiated by a collimated and polarized monochromatic incident radiation.

FIG. 6 represents an enlargement of a sectional view of a curved-surface cavity 41 of a chip 43 (the upper face of which is covered with a metal layer 42) which exhibits a tilt of an angle β and which is irradiated by a monochromatic collimated beam with a mean angle of incidence θ, which is linearly polarized according to the transverse magnetic TM direction.

In the case of a tilt β of the sensitive surface (in this case of the cavity) relative to the perpendicular to the mean plane of the sensitive surface, the mean plane being defined as the plane parallel to the inter-cavity planar surfaces, the reflected beam still has an angular width $\Delta\theta$ which is equal to $4\alpha$, but which is this time centered about the mean angle $\gamma'_{mean}$ (represented by $\theta'_2$ in FIG. 6) such that $\gamma'_{mean} = \theta - 2\beta$ for a concave surface.

According to one embodiment, the angle β is defined in the following way: $0° < \beta \leq 80°$, preferably $15° \leq \beta \leq 45°$.

It is thus possible, according to the invention, to adjust, for each of the zones, both the angular width studied (by virtue of the choice of the radius of curvature) and also the mean angle (i.e. $\theta_2$ or $\theta'_2$ represented in FIGS. 5 and 6 depending on whether or not the cavity is tilted) of this angular range, thus making it possible to adjust the measurement sensitivity for various species within the same chip, during the same experiment.

Thus, according to one particular embodiment, at least one of the zones has both a different radius of curvature and a different orientation compared with the other zones of the chip.

According to another embodiment, which can be combined with the preceding ones, at least one distance between the base and the inter-zone surfaces is different from the others.

Figure 7:
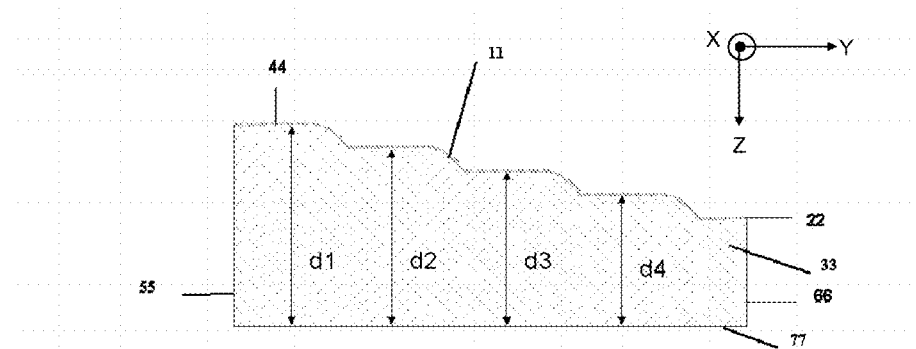
FIG. 7 represents a chip according to one embodiment of the invention which has different distances separating the planar surfaces between the protuberances and the base.

FIG. 7 represents a chip 33 of which the upper face 44, which is covered with a metal layer 22, is provided with curve-shaped protuberances 11. The side faces (55, 66) of the chip 33 are perpendicular to the base 77 and to the planar surfaces. The distances separating the planar surfaces between the protuberances (i.e. inter-protuberance surfaces) 11 and the base 77 are all different from one another, with d4<d3<d2<d1. In FIG. 7, the inter-zone surfaces are in multiple planes parallel to the plane (XY) (5 planes represented).

According to another particular embodiment, in the case where at least one of the zones is of a different nature than the others and/or exhibits a tilt of an angle β that is different from the others and/or at least one distance separating the base from the planar surfaces between the zones is different from the others, the zones may be of identical dimension and may have, for example, an identical radius of curvature R.

Indeed, according to the invention, it is sufficient for just one parameter to differ from one zone to another (nature, dimension, orientation, distance between base and interzone planar surfaces). The chip according to the invention can be produced by various methods, which necessarily comprise a step of fabricating the chip followed by a step of depositing at least one thin metal layer.

Among the fabrication methods, mention may be made of high-pressure injection, direct mechanical machining, hot stamping, plasma etching, photolithography or laser ablation.

Among the methods for depositing thin metal layers, mention may be made of sputtering, vacuum evaporation techniques, or cold deposition techniques.

The cold deposition techniques are of use in particular in the case of a plastic support since the plastic cannot withstand large increases in temperature.

Analysis Device

Figure 8:
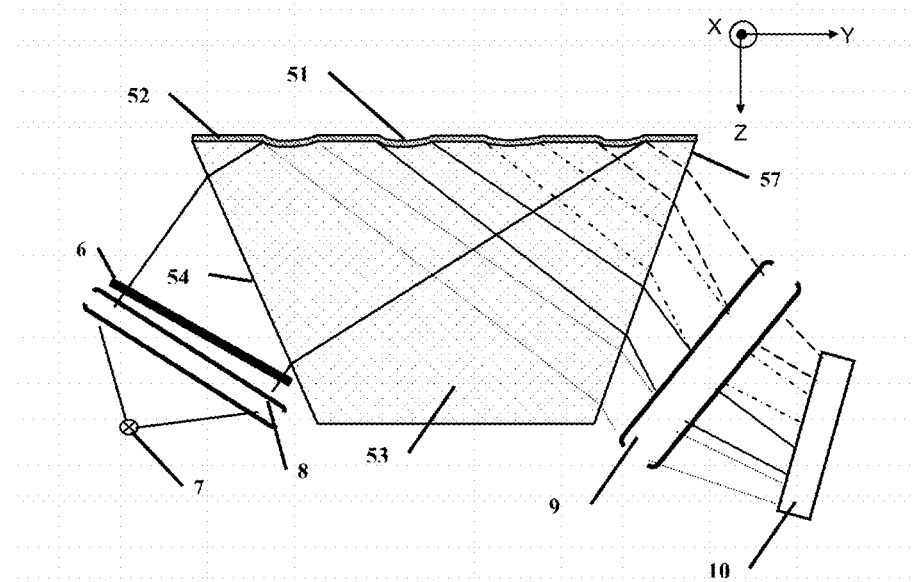
FIG. 8 represents a device comprising a microstructured chip which has identical distances between the inter-cavity surfaces and the base.
Figure 9:
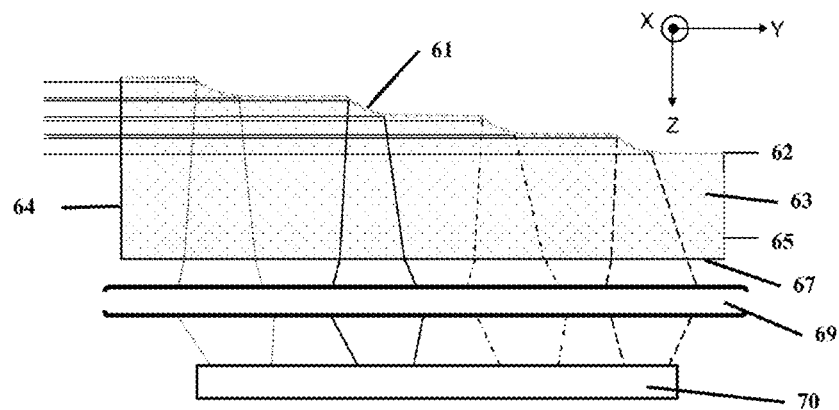
FIG. 9 represents a device comprising a microstructured chip which has different distances between the inter-cavity surfaces and the base.

FIGS. 8 and 9 represent different embodiments of measuring devices comprising the microstructured chip previously described.

Thus, another subject of the present invention is a device for SPR analysis comprising:
 a light source 7 intended to generate an incident beam;
 optionally an optical collimation system 8;
 a polarizing system 6;
 a microstructured chip (3; 33; 43; 53; 63) as previously described, placed in the optical path of said incident beam;
 optionally an optical imaging system (9; 69);
 a detector (10; 70).

According to one embodiment, the coupling between the energy of the incident beam and the surface wave of the metal surface of the chip is performed by the chip itself.

According to another embodiment, the coupling means is a prism, a waveguide or a diffraction network.

Thus, according to one particular embodiment, when the coupling is performed by a prism, the chip according to the invention is joined to said prism in such a way that the base of the chip is brought into contact with the upper face of the prism which does not have a metal surface by means of an index matching oil which is a method well-known to those skilled in the art.

According to another embodiment, the chip is joined to a waveguide.

According to yet another particular embodiment, the chip is joined to a diffraction network.

According to the invention, the source 7 may be, for example, a mercury vapor lamp, an incandescence lamp, a laser diode, a laser, a light-emitting diode (LED) or an organic light-emitting diode (OLED).

According to one preferred embodiment, the source 7 is a monochromatic LED. The term "monochromatic" is intended to mean an LED of which the mid-height width does not exceed 40 nm.

According to the invention, various wavelength ranges can be used, such as the visible range or the near infrared (IR) range.

According to one preferred embodiment, a wavelength of between 790 and 825 nm (near IR) is used.

According to the invention, the beam may be collimated. To do this, various techniques well-known to those skilled in the art may be used.

By way of example, use may be made, as optical collimation system 8, of a first convergent lens which makes it possible to focus the light emitted by the source 7 on a hole with a diameter Φ, said hole being in the focal plane of a convergent lens, thereby making it possible to generate the collimated beam.

According to one embodiment, the optical collimation system 8 is integrated into the source 7.

According to the invention, the polarizing system 6 makes it possible to work in transverse magnetic (or TM, or polarization-p) mode.

By way of example, mention may be made of a linear polarizer or a polarizing splitter cube.

According to one preferred embodiment, the polarizing system 6 makes it possible to easily switch from a TM polarization to a TE (transverse electric) polarization, and vice versa.

In order to avoid any movement of parts, this can be carried out using a liquid crystal strip, controlled by electric currents and voltages.

According to the invention, the detector (10; 70) may be a CCD or CMOS camera or may be a photodetector matrix.

According to one preferred embodiment, the cameras operate on 8, 10, 12 or 16 bits and preferably on 10 or 12 bits.

According to one embodiment, the device also comprises an optical imaging system (9; 69) which makes it possible to produce the image of the microstructured chip (3; 33; 43; 53; 63) on the detector (10; 70).

The optical imaging system (9; 69) must be sufficiently open to accept all the radiations stemming from the microstructured chip. Furthermore, the optical imaging system (9; 69) is chosen so that the images of two cavities or protuberances of the microstructured chip correspond to two different positions on the detector (10; 70).

Finally, advantageously, the optical system exhibits an enlargement which maximizes the number of useful pixels on the detector (10; 70).

By way of example of an optical imaging system (9; 69), mention may be made of 2 planar-convex lenses mounted afocally.

According to the invention, the face via which an incident radiation enters the chip is referred to as the entry face and the face via which the radiation reflected by the sensitive surface exits is referred to as the exit face.

In FIG. 8, the source 7 emits a monochromatic incident radiation, which is collimated by means of the collimation system 8 and polarized by means of the polarizer 6 before reaching the entry face 54 of the chip 53 (covered with a metal layer 52) under a given incidence. The radiation is refracted at its entry into the chip 53 and comes to be reflected on the cavities 51.

The imaging system 9, located after the exit face 57 of said chip 53, makes it possible to collect the intensity of the reflected radiations and to produce the image of the irradiated protuberances 51 on the detector 10.

The device represented in FIG. 9 comprises a chip 61 (covered with a metal layer 62) of which the side faces are perpendicular to the base and of which the distances between the surfaces separating the cavities 61 from the base are different from one another.

FIG. 9 represents an embodiment in which the incident radiation emitted by the source (not represented in FIG. 9) which reaches the entry face 64 (corresponding to the side face) perpendicularly, is not deflected when it passes through the chip 63, and irradiates all of the various cavities 61.

The imaging system 69 and the detector 70 are located after the exit face 67, which, in this embodiment, corresponds to the base of said chip 63, thus making it possible to collect the intensity of the reflected radiations and to produce the image of the irradiated cavities 61.

According to one embodiment, the optical imaging system (9; 69) can be directly integrated into the exit face (57; 67) of the chip (53; 63) in the form of a matrix of microlenses.

According to one preferred embodiment, the collimation system 8 and, optionally, the polarizer 6 are secured to the entry face (54; 64) and/or the optical imaging system (9; 69) and the detector (10; 70) are secured to the exit face (57; 67).

Method of Measurement

Another subject of the invention relates to a method of SPR measurement which comprises the following steps:

detecting an initial state (i) by irradiating the sensitive surface of at least two zones chosen from at least one cavity and/or at least one protuberance via the entry face of the microstructured chip by means of a previously polarized and optionally collimated monochromatic incident beam; and (ii) by simultaneously detecting the intensity of the radiations reflected by the sensitive surface of at least two of said zones, exiting via the exit face;

bringing at least one fluid into contact with the sensitive surface of at least two of said zones;

irradiating the sensitive surface of at least two of said zones, containing said fluid, via the entry face of the microstructured chip, by means of a previously polarized and optionally collimated monochromatic incident beam; and simultaneously detecting the intensity of the radiations reflected by the sensitive surface of at least two of said zones, exiting via the exit face, so as to continuously monitor, in real time, optical thickness modifications in at least two of said zones.

Another subject of the invention relates to a method of SPR measurement which comprises the following steps:

immobilizing ligands on the upper face, covered with a metal layer, of a microstructured chip as previously defined;

detecting an initial state (i) by irradiating the sensitive surface of at least two zones chosen from at least one cavity and/or at least one protuberance via the entry face of the microstructured chip by means of a previously polarized and optionally collimated monochromatic incident beam; and (ii) by simultaneously detecting the intensity of the radiations reflected by the sensitive surface of at least two of said zones, exiting via the exit face;

bringing at least one fluid into contact with the sensitive surface of at least two of said zones of said microstructured chip;

irradiating the sensitive surface of at least two of said zones containing said fluid, via the entry face of the microstructured chip, by means of a previously polarized and optionally collimated monochromatic incident beam; and simultaneously detecting the intensity of the radiations reflected by the sensitive surface of at least two of said zones, exiting via the exit face, so as to continuously monitor, in real time, optical thickness modifications in at least two of said zones.

According to the invention, the immobilization of the ligands on the upper surface can be carried out with various techniques known to those skilled in the art, for instance immobilization by covalent chemical bonding or by electrocopolymerization of pyrrole on the metal surface.

The term "fluid" is intended to mean a gas or a liquid.

According to one preferred embodiment of the invention, the fluid comprises at least one biological species.

These methods of measurement are suitable for measuring, in a nonlimiting manner, conformational variations in molecules immobilized on a surface, molecular interactions, optical indices of fluids (gases or liquids), the quality of a surface (parallelism, microscopic roughness, quality of a thin-layer deposit) or of the presence of metal nanobeads in proximity to the surface.

These methods of measurement also make it possible to measure external parameters such as the optical index of the external medium, which makes it possible to work back to the value of the limiting angle of refraction.

According to one embodiment, the incident beam enters perpendicularly via the entry face 64 of the chip 63.

The detection of the intensity of the reflected radiations in the angular range $\Delta\theta$ (or $\Delta\theta'$) by the detector (10; 70) makes it possible to generate all or part of the plasmon curve, the principal zones of interest of which are the following:
- the minimum plasmon sensitivity;
- the angular range in which the sensitivity is highest (i.e. where the derivative of the plasmon is the greatest), also referred to as "flank of the plasmon";
- the zone in the area of the limiting angle of refraction (where things change from a system of refraction to a system of total reflection).

Figure 10:
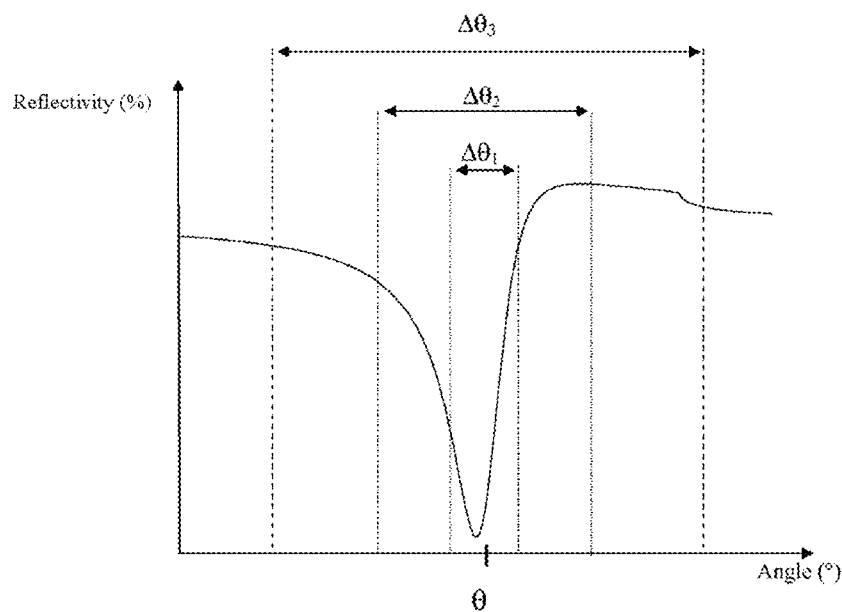
FIG. 10 shows a representative plasmon curve of various angular ranges studied (without tilt).
Figure 11:
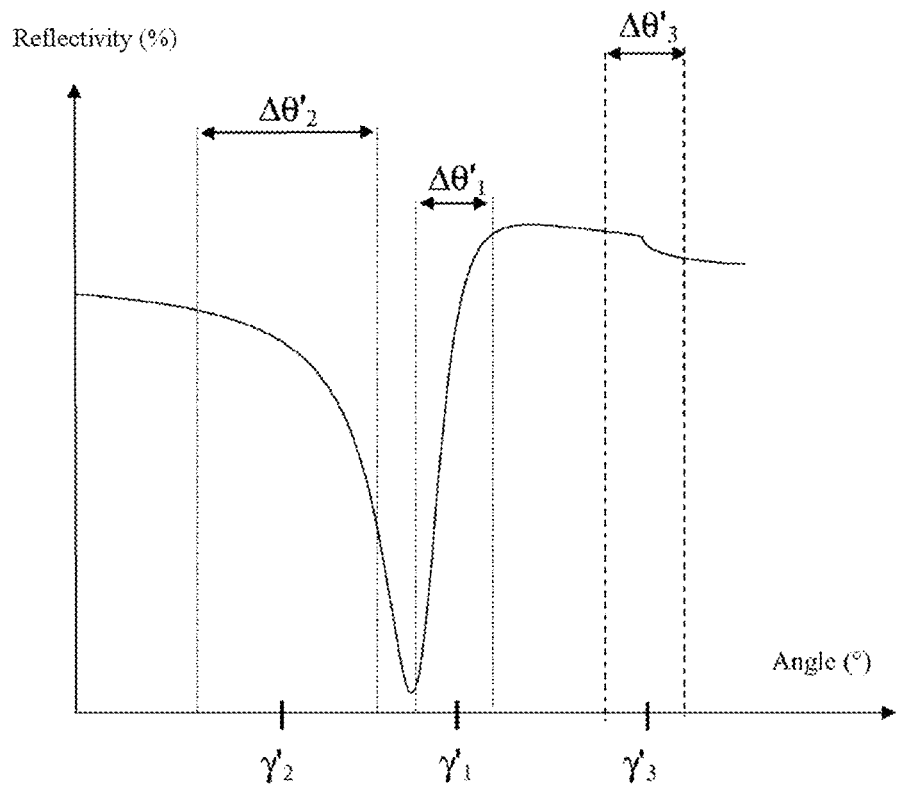
FIG. 11 shows a representative plasmon curve of various angular ranges studied (with tilt).

FIGS. 10 and 11 represent a plasmon curve for 3 cavities and/or protuberances having different angular study ranges ($1^{st}$ cavity and/or protuberance having an angular range $\Delta\theta_1$ for FIG. 10 and $\Delta\theta'_1$ for FIG. 11, $2^{nd}$ cavity and/or protuberance having an angular range $\Delta\theta_2$ for FIG. 10 and $\Delta\theta'_2$ for FIG. 11 and $3^{rd}$ cavity and/or protuberance having an angular range $\Delta\theta_3$ for FIG. 10 and $\Delta\theta'_3$ for FIG. 11).

FIG. 10 represents the angular ranges of 3 cavities and/or protuberances when $\beta=0$ (without tilt), while FIG. 11 represents the angular ranges of 3 cavities and/or protuberances when $\beta\neq 0$ (with tilt).

In FIG. 10, i.e. when $\beta=0$ (without tilt), the 3 angular ranges studied are centered on the angle $\theta$. The width of each of the ranges is defined by the angle at the apex $2\alpha$ and the radius of curvature R of each of the cavities and/or protuberances. The choice of the angle $\theta$ is therefore essential for observing all the zones of interest as well as possible. It is thus possible, according to the radius of curvature of the zones studied, to explore a more or less large angular range of the plasmon curve. In the case where the zones do not exhibit any tilt $\beta$ (this is the case for FIG. 10), this angular range will always be centered on the same value $\theta$.

In FIG. 11, i.e. when $\beta\neq 0$ (with tilt), the three angular ranges $\Delta\theta'_1$, $\Delta\theta'_2$ and $\Delta\theta'_3$ are centered respectively on the angles $\gamma'_1$, $\gamma'_2$ and $\gamma'_3$, said angles $\gamma'_1$, $\gamma'_2$ and $\gamma'_3$ each being defined by different angles $\beta$. In this situation (with tilt), the angular ranges are not centered on the same value.

It is thus possible to explore a variable angular range of the plasmon curve while having an incident beam at a single angle, thus making it possible not to need the mobile parts normally used for performing an angular rotation of the incident beam.

According to another embodiment, the method of measurement also comprises a step in which an image of the cavities and/or protuberances of the chip is produced.

Figure 12:
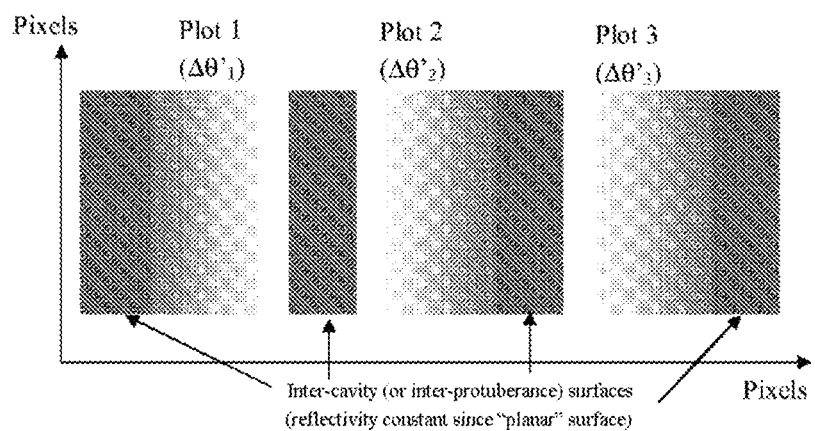
FIG. 12 represents an example of an image on a camera of three cavities of a microstructured chip according to the invention.

FIG. 12 represents the image of the 3 cavities and/or protuberances (plasmon curve of FIG. 11) on a matrix detector in which the dark band between the luminous bands (light gray) represents the inter-zone surfaces (i.e. inter-cavity and/or inter-protuberance and/or inter-cavity-protuberance surfaces) which have a constant reflectivity since they are planar surfaces.

According to the invention, it is thus possible, knowing the incident angle $\theta$ which is constant and fixed by the architecture of the optical system (since no mechanical part is moving), to choose the angular range $\Delta\theta$ that will optionally be imaged on the detector (by choosing the radius of curvature R and the angle $\alpha$, or the radius of curvature R and the diameter d, since a and d are deduced from one another by virtue of the radius of curvature R) and the mean angle $\gamma'_{mean}$ (with the choice of the tilt $\beta$) of the microstructure according to the various species to be analyzed with $\gamma'_{mean}=\theta+2\beta$ for a convex surface). This choice can be made for each of the cavities and/or protuberances, thereby making it possible to adapt to several types of species immobilized on the same chip.

Likewise, the choice can be made according to the type of species that will interact with the species previously immobilized on the chip: it is thus possible to "adapt" each of the cavities and/or protuberances to the species sought.

Thus, another subject of the invention relates to the use of the device according to the invention for measuring biomolecular interactions.

The invention is illustrated by means of the examples which are given solely by way of illustration and are not limiting.

Figure 13:
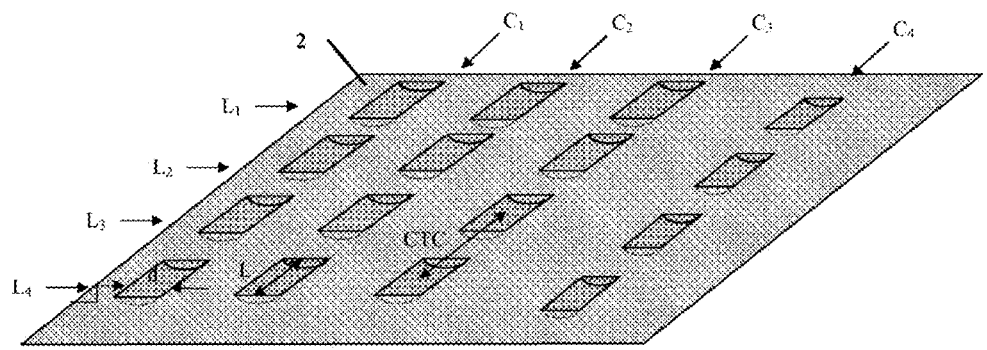
FIG. 13 represents a chip according to the invention comprising 16 cavities, at least one of which is different from the others.

Example 1: Protein Chip—Monitoring and Correction of the Index of the External Medium in Real Time in Interaction Kinetics A microstructured chip made of polycarbonate (PC) comprising 16 cavities is represented in FIG. 13.

A layer of gold which has a thickness of 48 nm was deposited by sputtering on the upper face of said chip in order to obtain a plasmon effect.

In TM polarization, the minimum reflectivity is obtained around the angle $\theta=28°$.

The 16 cavities are distributed according to a regular matrix of 4×4 semi-cylindrical surfaces having a diameter d=500 µm and a length L=500 µm, each one spaced out by a center-to-center (CTC) distance of 1 mm.

Four different species were covalently immobilized by virtue of an electropolymerization of a film of polypyrrole functionalized with the ligands of interest.

Thus, the following species present in the cavities are:
- on line $L_1$: monoclonal anti-mouse antibodies,
- on line $L_2$: monoclonal antibodies directed against human chorionic gonadotropin hormone (hCG, involved as a biomarker in several cancer pathologies),
- on line $L_3$: monoclonal antibodies directed against the bacterium *Listeria monocytogenes,*
- on line $L_4$: BSA (bovin serum albumin).

The chip is irradiated with a polarized, collimated and monochromatic incident radiation and the intensity of the radiations reflected by the cavities is detected by a CMOS detector.

The radius of curvature of the semi-cylindrical surfaces of columns $C_1$, $C_2$ and $C_3$ is 9.5 mm (equivalent to an angular study zone $\Delta\theta_a$ on the plasmon curve of approximately 3°) and the cavities of column $C_4$ have a radius of curvature of 1.9 mm (equivalent to an angular study zone $\Delta\theta_b$ of approximately 15°). The angular ranges $\Delta\theta_a$ and $\Delta\theta_b$ correspond respectively to the angular ranges $\Delta\theta_1$ and $\Delta\theta_3$ in FIG. 10.

A liquid with an unknown optical index, containing hCG proteins, is brought into contact with the chip in the cavities. A characteristic variation in the signal is observed as a function of time on the cavities of line $L_2$, but not on the others since a specific interaction takes place on the anti-hCG monoclonal antibodies and not on the other immobilized proteins.

Furthermore, since the cavity located at $(L_2, C_4)$ has a radius of curvature such that the entire plasmon curve can be visualized on the detector, the angular value of the limiting angle of refraction can be easily determined and it is thus possible to deduce the unknown index of the liquid medium.

Thus, knowing this index, it is possible to accurately determine the variation in the signal on the cavities located at $(L_2, C_1)$, $(L_2, C_2)$ and $(L_2, C_3)$, by decorrelating the variation in signal associated with the external medium from the variation in signal associated with the attachment of hCG proteins to the anti-hCG monoclonal antibodies.

Example 2: Chip for Studying Shiga Toxin-Producing *Escherichia coli* Bacteria

In this example, the presence of shiga toxin-producing *Escherichia coli* (STEC) bacteria in a sample stemming from the food-processing industry was studied.

Examples of bacteria of this category are the O157:H7, O26:H11 or else O103:H2 strains. The bacteria of this type and the shiga toxins that they produce are responsible for severe intestinal problems, which may be life-threatening. The size and the molecular weight of these shiga toxins (a few nanometers in diameter and a molecular weight of approximately 68 kDa) is very different from that of an *Escherichia coli* bacterium (approximately 10 million times heavier). Consequently, the plasmon signals for the attachment of these two types of families are very different. With conventional SPR devices, it is not therefore possible to study both these bacteria and these toxins in the same experiment and in real time. This is because, in the case of the attachment of bacteria, the curve will shift angularly by close to 0.1°, whereas it will only move by less than 0.01° in the case of toxins (which is not easily detectable by conventional SPR methods).

This example demonstrates that, by using a microstructured chip according to the invention which has a particular architecture, it is possible to study these two biological species of different sizes during a single experiment.

A chip made of polycarbonate, comprising two semi-cylindrical protuberances, 600 µm in diameter and 800 µm long, is produced.

The upper face of said chip is covered with a layer of chromium having a thickness of 2 nm and with a layer of gold having a thickness of 48 nm, both deposited by sputtering in order to obtain a plasmon effect.

The first protuberance exhibits a zero tilt ($\beta=0$) and the second protuberance exhibits a tilt of value $\beta=0.5°$.

The chip is irradiated with a polarized, collimated and monochromatic incident radiation and the intensity of the radiations reflected by the sensitive surface of the protuberances is detected by a CCD detector.

The mean angle of incidence of the optical system is mechanically fixed by the architecture of the system and is equal to 26.5°.

Figure 14:
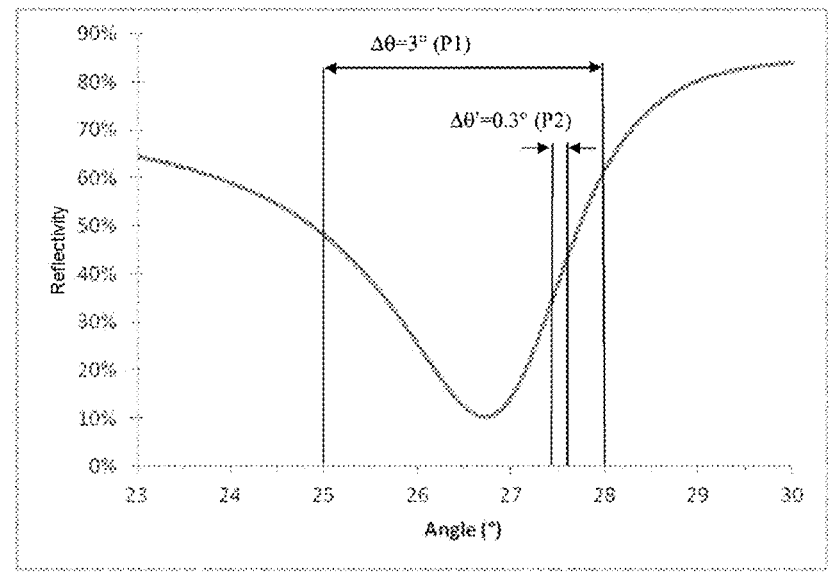
FIG. 14 represents the percentage reflectivity as a function of the angle of incidence θ.

The radius of curvature of the two protuberances is also different: 11.5 mm for the first protuberance (corresponding to an angular study range $\Delta\theta$ of 3°) and 100 mm for the second (which corresponds to an angular analysis range $\Delta\theta'$ of 0.3°) (FIG. 14).

Monoclonal antibodies directed against the O157:H7 bacterium are covalently and uniformly immobilized on the first protuberance, and monoclonal antibodies specifically directed against the shiga toxins that the bacterium secretes are immobilized on the second protuberance.

The two plasmon curves generated from these two protuberances exhibit the same plasmon resonance angle (approximately 26.7°), before reaction.

When a mixture containing a large amount (i.e. concentrations greater than $10^5$ bacteria per ml) of O157:H7 bacteria is brought into contact with the sensitive surface of the chip (in other words on the protuberances), some of them interact specifically with the antibodies of the first protuberance. Since bacteria are molecules that are detected well by SPR (owing to their heavy weight), the plasmon curve shifts sufficiently for this shift to be picked up very well by the detector imaging the first protuberance. Moreover, this bacterium also secretes shiga toxins during the same experiment.

Figure 15:
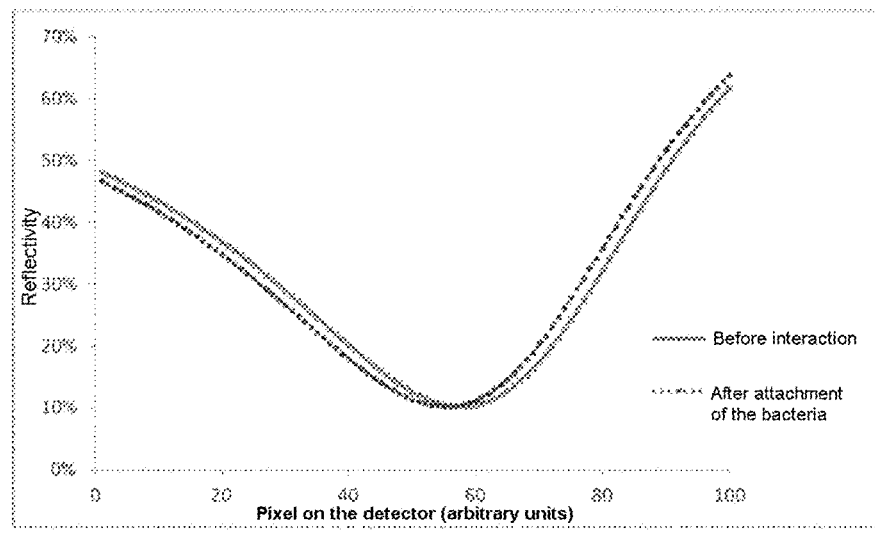
FIG. 15 represents the plasmon curves before and after attachment of the *Escherichia coli* bacterium on the protuberances functionalized with ligands specific for the bacterium.
Figure 16:
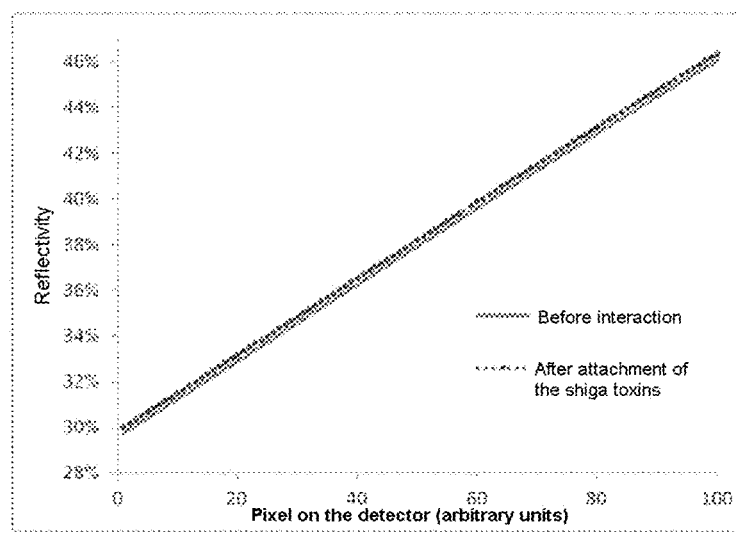
FIG. 16 represents the plasmon curves before and after attachment of the shiga toxins on the protuberances functionalized with ligands specific for the shiga toxins.

The second protuberance exhibits a slight tilt ($\beta=0.5°$) and a much smaller angular width studied ($\Delta\theta'=0.3°$). Thus, the measurement sensitivity of the second protuberance is greater and it is possible to detect shiga toxins which bind to the antibodies of the second protuberance. FIGS. 15 and 16 represent the signals obtained on the detector for the two protuberances respectively without tilt and with tilt, before and after interaction of the antibodies immobilized on each of the protuberances with, respectively, the bacteria and the toxins.

Thus, this example demonstrates that the chip according to the invention makes it possible to adjust the measurement dynamics and sensitivity to the species to be measured during a single experiment.

Example 3: Particular Configuration of a Microstructured Chip Joined to a Prism

Figure 17:
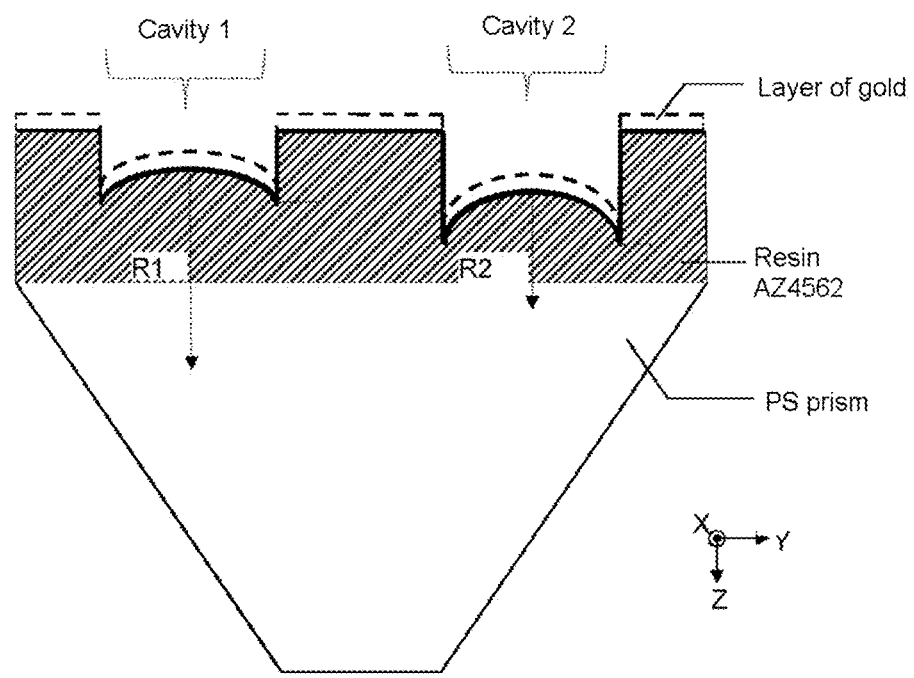
FIG. 17 represents a sectional view of a chip according to one embodiment in which the chip is joined to a prism.

A section along the plane (YZ) of a microstructured chip comprising 2 cavities is represented in FIG. 17. The two cavities are produced in the form of gutters along the entire length of the chip (see FIG. 4).

The chip (represented by hatching in FIG. 17) is produced directly on a polystyrene (PS) prism. To do this, a layer of photosensitive resin of AZ4562 type from the company Clariant, 10 µm thick, was deposited beforehand on a PS prism by spin coating. This layer was then insolated in the +X direction by light so as to reproduce the cavities in FIG. 17. A layer of gold, 47 nm thick, was then deposited by vacuum evaporation on the upper face of the previously insolated resin.

The 2 cavities are described in the plane (YZ) and defined by two parallel straight lines separated by a curve, said curve having a radius of curvature R of convex shape (in other words, a radius of curvature along the +Z axis). According to this example, the cavities have a different radius of curvature (R1≠R2) in order for it to be possible to observe 2 different angular ranges of the plasmon curve.

The invention claimed is:

1. A microstructured chip (3; 33; 43; 53; 63) for surface plasmon resonance (SPR) analysis, said microstructured chip comprising:
   a solid consisting of a base (5; 77), an upper face (4; 44), and at least one side face (55; 66);
   a metal layer (2; 22; 42; 52; 62) that covers at least one part of the upper face; and
   at least a first zone and a second zone provided in said upper face (4; 44), each of the first and second zones having a curved surface of micrometric size intended to receive species to be analyzed, the first and second zones having at least two of i) a length dimension, ii) a width dimension, and iii) a height dimension ranging from 1 μm to 1000 μm, said at least first and second zones having a form of at least one of the group consisting of a cavity and a protuberance (1; 11; 41; 51; 61), said first and second zones are adjacent each other and separated from one another by an adjacent planar surface, and said first zone is different from said second zone based on at least one of the group consisting of i) the first zone having the form of the cavity and the second zone having the form of the protuberance, ii) the first zone having a radius of curvature ("R") different from a corresponding radius of curvature ("R") of the second zone, iii) the first zone having an orientation different from a corresponding orientation of the second zone such that a tilt of an angle (β1') of the first zone relative to the adjacent planar surface is different from a tilt of an angle (β2') of the second zone relative to the adjacent planar surface, and iv) the first zone having a distance between an inter-zone surface and the base of the chip different from a corresponding distance between the inter-zone and base of the chip of the second zone, wherein, each of the at least first and second zones (1; 11; 41; 51; 61) are in the form of the protuberance, the protuberance having a convex curved surface with respect to the adjacent planar surface, a radius of curvature ("R") of the convex curved surface being between 0.1 and 600 mm, the radius of curvature ("R") of the convex curved surface of the first zone is the same as the radius of curvature ("R") of the convex curved surface of the second zone, and said first zone is different from said second zone based on at least one of the group consisting of i) the first zone having an orientation different from a corresponding orientation of the second zone such that a tilt of an angle (β1') of the first zone relative to the adjacent planar surface is different from a tilt of an angle (β2') of the second zone relative to the adjacent planar surface, and ii) the first zone having a distance between an inter-zone surface and the base of the chip different from a corresponding distance between the inter-zone and base of the chip of the second zone.

2. A microstructured chip (3; 33; 43; 53; 63) for surface plasmon resonance (SPR) analysis, said microstructured chip comprising:

a solid consisting of a base (5; 77), an upper face (4; 44), and at least one side face (55; 66);

a metal layer (2; 22; 42; 52; 62) that covers at least one part of the upper face; and at least a first zone and a second zone provided in said upper face (4; 44), each of the first and second zones having a curved surface of micrometric size intended to receive species to be analyzed, the first and second zones having at least two of i) a length dimension, ii) a width dimension, and iii) a height dimension ranging from 1 μm to 1000 μm, said at least first and second zones having a form of at least one of the group consisting of a cavity and a protuberance (1; 11; 41; 51; 61), said first and second zones are adjacent each other and separated from one another by an adjacent planar surface, and said first zone is different from said second zone based on at least one of the group consisting of i) the first zone having the form of the cavity and the second zone having the form of the protuberance, ii) the first zone having a radius of curvature ("R") different from a corresponding radius of curvature ("R") of the second zone, iii) the first zone having an orientation different from a corresponding orientation of the second zone such that a tilt of an angle (β1') of the first zone relative to the adjacent planar surface is different from a tilt of an angle (β2') of the second zone relative to the adjacent planar surface, and iv) the first zone having a distance between an inter-zone surface and the base of the chip different from a corresponding distance between the inter-zone and base of the chip of the second zone, wherein, each of the at least first and second zones (1; 11; 41; 51; 61) are in the form of the protuberance having a convex curved surface with respect to the adjacent planar surface, a radius of curvature ("R") of the convex curved surface being between 0.1 and 600 mm, and the radius of curvature ("R") of the convex curved surface of the first zone is different from the radius of curvature ("R") of the convex curved surface of the second zone.

3. A microstructured chip (3; 33; 43; 53; 63) for surface plasmon resonance (SPR) analysis, said microstructured chip comprising:

a solid consisting of a base (5; 77), an upper face (4; 44), and at least one side face (55; 66);

a metal layer (2; 22; 42; 52; 62) that covers at least one part of the upper face; and at least a first zone and a second zone provided in said upper face (4; 44), each of the first and second zones having a curved surface of micrometric size intended to receive species to be analyzed, the first and second zones having at least two of i) a length dimension, ii) a width dimension, and iii) a height dimension ranging from 1 μm to 1000 μm, said at least first and second zones having a form of at least one of the group consisting of a cavity and a protuberance (1; 11; 41; 51; 61), said first and second zones are adjacent each other and separated from one another by an adjacent planar surface, and said first zone is different from said second zone based on at least one of the group consisting of i) the first zone having the form of the cavity and the second zone having the form of the protuberance, ii) the first zone having a radius of curvature ("R") different from a corresponding radius of curvature ("R") of the second zone, iii) the first zone having an orientation different from a corresponding orientation of the second zone such that a tilt of an angle (β1') of the first zone relative to the adjacent planar surface is different from a tilt of an angle (β2') of the second zone relative to the adjacent planar surface, and iv) the first zone having a distance between an inter-zone surface and the base of the chip different from a corresponding distance between the inter-zone and base of the chip of the second zone, wherein, each of the at least first and second zones comprise a curved surface with respect to the adjacent planar surface, a radius of curvature ("R") of the curved surface being between 0.1 and 600 mm, and the radius of curvature ("R") each of the at least first and second zones (1; 11; 41; 51; 61) is identical.

4. A microstructured chip (3; 33; 43; 53; 63) for surface plasmon resonance (SPR) analysis, said microstructured chip comprising:

a solid consisting of a base (5; 77), an upper face (4; 44), and at least one side face (55; 66);

a metal layer (2; 22; 42; 52; 62) that covers at least one part of the upper face; and at least a first zone and a second zone provided in said upper face (4; 44), each of the first and second zones having a curved surface of micrometric size intended to receive species to be analyzed, the first and second zones having at least two of i) a length dimension, ii) a width dimension, and iii) a height dimension ranging from 1 µm to 1000 µm, said at least first and second zones having a form of at least one of the group consisting of a cavity and a protuberance (1; 11; 41; 51; 61), said first and second zones are adjacent each other and separated from one another by an adjacent planar surface, and said first zone is different from said second zone based on at least one of the group consisting of i) the first zone having the form of the cavity and the second zone having the form of the protuberance, ii) the first zone having a radius of curvature ("R") different from a corresponding radius of curvature ("R") of the second zone, iii) the first zone having an orientation different from a corresponding orientation of the second zone such that a tilt of an angle (β1') of the first zone relative to the adjacent planar surface is different from a tilt of an angle (β2') of the second zone relative to the adjacent planar surface, and iv) the first zone having a distance between an inter-zone surface and the base of the chip different from a corresponding distance between the inter-zone and base of the chip of the second zone, wherein, the first zone is in the form of the cavity comprising a concave curved surface with respect to the adjacent planar surface, a radius of curvature ("R") of the concave curved surface being between 0.1 and 600 mm, and the second zone is in the form of the protuberance having a convex curved surface with respect to the adjacent planar surface, a radius of curvature ("R") of the convex curved surface being between 0.1 and 600 mm.

5. The microstructured chip according to claim 4, wherein the first and second zones are covered with the metal layer.

6. A microstructured chip (3; 33; 43; 53; 63) for surface plasmon resonance (SPR) analysis, said microstructured chip comprising:

a solid consisting of a base (5; 77), an upper face (4; 44), and at least one side face (55; 66);

a metal layer (2; 22; 42; 52; 62) that covers at least one part of the upper face; and at least a first zone and a second zone provided in said upper face (4; 44), each of the first and second zones having a curved surface of micrometric size intended to receive species to be analyzed, the first and second zones having at least two of i) a length dimension, ii) a width dimension, and iii) a height dimension ranging from 1 µm to 1000 µm, said at least first and second zones having a form of at least one of the group consisting of a cavity and a protuberance (1; 11; 41; 51; 61), said first and second zones are adjacent each other and separated from one another by an adjacent planar surface, and said first zone is different from said second zone based on at least one of the group consisting of i) the first zone having the form of the cavity and the second zone having the form of the protuberance, ii) the first zone having a radius of curvature ("R") different from a corresponding radius of curvature ("R") of the second zone, iii) the first zone having an orientation different from a corresponding orientation of the second zone such that a tilt of an angle (β1') of the first zone relative to the adjacent planar surface is different from a tilt of an angle (β2') of the second zone relative to the adjacent planar surface, and iv) the first zone having a distance between an inter-zone surface and the base of the chip different from a corresponding distance between the inter-zone and base of the chip of the second zone, wherein, each of the at least first and second zones (1; 11; 41; 51; 61) are in the form of the cavity comprising a concave curved surface with respect to the adjacent planar surface, a radius of curvature ("R") of the concave curved surface being between 0.1 and 600 mm, the radius of curvature ("R") of the concave curved surface of the first zone is the same as the radius of curvature ("R") of the concave curved surface of the second zone, and said first zone is different from said second zone based on at least one of the group consisting of i) the first zone having an orientation different from a corresponding orientation of the second zone such that a tilt of an angle (β1') of the first zone relative to the adjacent planar surface is different from a tilt of an angle (β2') of the second zone relative to the adjacent planar surface, and ii) the first zone having a distance between an inter-zone surface and the base of the chip different from a corresponding distance between the inter-zone and base of the chip of the second zone.

7. A microstructured chip (3; 33; 43; 53; 63) for surface plasmon resonance (SPR) analysis, said microstructured chip comprising:

a solid consisting of a base (5; 77), an upper face (4; 44), and at least one side face (55; 66);

a metal layer (2; 22; 42; 52; 62) that covers at least one part of the upper face; and at least a first zone and a second zone provided in said upper face (4; 44), each of the first and second zones having a curved surface of micrometric size intended to receive species to be analyzed, the first and second zones having at least two of i) a length dimension, ii) a width dimension, and iii) a height dimension ranging from 1 µm to 1000 µm, said at least first and second zones having a form of at least one of the group consisting of a cavity and a protuberance (1; 11; 41; 51; 61), said first and second zones are adjacent each other and separated from one another by an adjacent planar surface, and said first zone is different from said second zone based on at least one of the group consisting of i) the first zone having the form of the cavity and the second zone having the form of the protuberance,
ii) the first zone having a radius of curvature ("R") different from a corresponding radius of curvature ("R") of the second zone,
iii) the first zone having an orientation different from a corresponding orientation of the second zone such that a tilt of an angle ($\beta1'$) of the first zone relative to the adjacent planar surface is different from a tilt of an angle ($\beta2'$) of the second zone relative to the adjacent planar surface, and
iv) the first zone having a distance between an inter-zone surface and the base of the chip different from a corresponding distance between the inter-zone and base of the chip of the second zone, wherein,
each of the at least first and second zones (1; 11; 41; 51; 61) are in the form of the cavity and have a concave curved surface with respect to the adjacent planar surface, a radius of curvature ("R") of the concave curved surface being between 0.1 and 600 mm, and
the radius of curvature ("R") of the concave curved surface of the first zone is different from the radius of curvature ("R") of the concave curved surface of the second zone.

8. A microstructured chip (3; 33; 43; 53; 63) for surface plasmon resonance (SPR) analysis, said microstructured chip comprising:
- a solid consisting of a base (5; 77), an upper face (4; 44), and at least one side face (55; 66);
- a metal layer (2; 22; 42; 52; 62) that covers at least one part of the upper face; and
- at least a first zone and a second zone provided in said upper face (4; 44), each of the first and second zones having a curved surface of micrometric size intended to receive species to be analyzed, the first and second zones having at least two of i) a length dimension, ii) a width dimension, and iii) a height dimension ranging from 1 μm to 1000 μm, said at least first and second zones having a form of at least one of the group consisting of a cavity and a protuberance (1; 11; 41; 51; 61),
said first and second zones are adjacent each other and separated from one another by an adjacent planar surface, and
said first zone is different from said second zone based on at least one of the group consisting of
i) the first zone having the form of the cavity and the second zone having the form of the protuberance,
ii) the first zone having a radius of curvature ("R") different from a corresponding radius of curvature ("R") of the second zone,
iii) the first zone having an orientation different from a corresponding orientation of the second zone such that a tilt of an angle ($\beta1'$) of the first zone relative to the adjacent planar surface is different from a tilt of an angle ($\beta2'$) of the second zone relative to the adjacent planar surface, and
iv) the first zone having a distance between an inter-zone surface and the base of the chip different from a corresponding distance between the inter-zone and base of the chip of the second zone,
wherein the tilt of at least one of said first and second zones (1; 11; 41; 51; 61) is greater than 0° and no more than 80°,
wherein, the first zone has an orientation different from a corresponding orientation of the second zone such that a tilt of an angle ($\beta1'$) of the first zone relative to the adjacent planar surface is different from a tilt of an angle ($\beta2'$) of the second zone relative to the adjacent planar surface, and
wherein each of the at least first and second zones comprise a curved surface with respect to the adjacent planar surface, a radius of curvature ("R") of the curved surface being between 0.1 and 600 mm.

\* \* \* \* \*